United States Patent
Katra

(10) Patent No.: US 12,262,991 B2
(45) Date of Patent: *Apr. 1, 2025

(54) SYSTEM AND METHOD FOR NON-INVASIVE MONITORING OF HEMATOCRIT CONCENTRATION

(71) Applicant: Medtronic Monitoring, Inc., San Jose, CA (US)

(72) Inventor: Rodolphe Katra, Blaine, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 273 days.

This patent is subject to a terminal disclaimer.

(21) Appl. No.: 17/452,190

(22) Filed: Oct. 25, 2021

(65) Prior Publication Data
US 2022/0039705 A1  Feb. 10, 2022

Related U.S. Application Data

(63) Continuation of application No. 15/866,118, filed on Jan. 9, 2018, now Pat. No. 11,154,224.

(51) Int. Cl.
*A61B 5/1455* (2006.01)
*A61B 5/00* (2006.01)
(Continued)

(52) U.S. Cl.
CPC ........ *A61B 5/14546* (2013.01); *A61B 5/0071* (2013.01); *A61B 5/14535* (2013.01);
(Continued)

(58) Field of Classification Search
CPC .............. A61B 5/1455; A61B 5/14551; A61B 5/14552; A61B 5/14532; A61B 5/14546;
(Continued)

(56) References Cited

U.S. PATENT DOCUMENTS

| 5,372,136 A | 12/1994 | Steuer et al. |
| 5,377,674 A | 1/1995 | Kuestner et al. |

(Continued)

FOREIGN PATENT DOCUMENTS

| WO | 9313706 A1 | 7/1993 |
| WO | 0122869 A1 | 4/2001 |

(Continued)

OTHER PUBLICATIONS

Anand, et al., "Anemia and Change in Hemoglobin Over Time Related to Mortality and Morbidity in Patients With Chronic Heart Failure", Results From Val-HeFT. Circ., Aug. 23, 2005; 112: 1121-1127.

(Continued)

*Primary Examiner* — Chu Chuan Liu
(74) *Attorney, Agent, or Firm* — Shumaker & Sieffert, P.A.

(57) ABSTRACT

A method of non-invasively monitoring hematocrit levels includes monitoring a first emission response to the light provided at the first excitation wavelength, wherein the first emission response is monitored at a first wavelength and monitoring a second emission response to the light provided at the first excitation wavelength, wherein the second emission response is monitored at a second wavelength. A ratiometric value is calculated based on a ratio of the first emission response to the second emission response, wherein the ratiometric value corresponds with hematocrit level of the patient.

18 Claims, 8 Drawing Sheets

(51) Int. Cl.
  *A61B 5/145* (2006.01)
  *A61B 5/02* (2006.01)
(52) U.S. Cl.
  CPC .......... *A61B 5/1455* (2013.01); *A61B 5/6826* (2013.01); *A61B 5/0082* (2013.01); *A61B 5/02028* (2013.01); *A61B 2562/0233* (2013.01)
(58) Field of Classification Search
  CPC . A61B 5/0071; A61B 5/14535; A61B 5/1459; A61B 2562/0233
  See application file for complete search history.

(56) References Cited

U.S. PATENT DOCUMENTS

| | | | |
|---|---|---|---|
| 5,377,675 A | 1/1995 | Ruskewicz et al. | |
| 5,551,422 A | 9/1996 | Simonsen et al. | |
| 5,692,503 A | 12/1997 | Kuestner et al. | |
| 5,692,504 A | 12/1997 | Essenpreis et al. | |
| 6,064,474 A | 5/2000 | Lee et al. | |
| 6,526,298 B1 | 2/2003 | Khalil et al. | |
| 6,606,509 B2 | 8/2003 | Schmitt | |
| 6,728,560 B2 | 4/2004 | Kollias et al. | |
| 7,139,598 B2 | 11/2006 | Hull et al. | |
| 8,078,243 B2 | 12/2011 | Ediger et al. | |
| 8,121,671 B2 | 2/2012 | Hull et al. | |
| 8,131,332 B2 | 3/2012 | Maynard et al. | |
| 8,172,459 B2 | 5/2012 | Abreu | |
| 8,238,993 B2 | 8/2012 | Maynard et al. | |
| 8,320,981 B1 | 11/2012 | Mayer et al. | |
| 8,346,332 B2 | 1/2013 | Kuhn et al. | |
| 8,480,581 B2 | 7/2013 | Zhang et al. | |
| 8,571,620 B2 | 10/2013 | Cinbis et al. | |
| 8,676,283 B2 | 3/2014 | Matter et al. | |
| 11,039,768 B2 | 6/2021 | Katra | |
| 11,051,727 B2 | 7/2021 | Katra | |
| 11,154,224 B2 | 10/2021 | Katra | |
| 2002/0038079 A1 | 3/2002 | Steuer et al. | |
| 2002/0082489 A1 | 6/2002 | Casciani et al. | |
| 2002/0165439 A1 | 11/2002 | Schmitt | |
| 2003/0009090 A1* | 1/2003 | Jeon | A61B 5/14551 600/323 |
| 2003/0018241 A1 | 1/2003 | Mannheimer | |
| 2004/0225207 A1 | 11/2004 | Bae et al. | |
| 2006/0195022 A1 | 8/2006 | Trepagnier et al. | |
| 2007/0156036 A1 | 7/2007 | Laurent et al. | |
| 2008/0214911 A1 | 9/2008 | Forstner et al. | |
| 2009/0118666 A1 | 5/2009 | Blomqvist et al. | |
| 2010/0099964 A1 | 4/2010 | O'Reilly et al. | |
| 2010/0110416 A1 | 5/2010 | Barrett et al. | |
| 2010/0185252 A1 | 7/2010 | Björling et al. | |
| 2010/0249865 A1* | 9/2010 | Zhang | A61B 5/14535 607/17 |
| 2010/0268090 A1 | 10/2010 | Rubinstein et al. | |
| 2010/0280499 A1 | 11/2010 | Yodfat et al. | |
| 2010/0298675 A1 | 11/2010 | Al-Ali et al. | |
| 2012/0277546 A1 | 11/2012 | Soykan et al. | |
| 2013/0178724 A1 | 7/2013 | Ting et al. | |
| 2013/0217984 A1 | 8/2013 | Graaff et al. | |
| 2015/0073243 A1 | 3/2015 | Taub et al. | |
| 2015/0201839 A1 | 7/2015 | Kang et al. | |
| 2015/0245799 A1 | 9/2015 | Gretz et al. | |
| 2016/0061810 A1 | 3/2016 | Kim et al. | |
| 2016/0367188 A1 | 12/2016 | Malik et al. | |
| 2016/0371452 A1 | 12/2016 | Andrum et al. | |
| 2019/0209055 A1 | 7/2019 | Katra | |
| 2019/0209060 A1 | 7/2019 | Katra | |
| 2021/0307661 A1 | 10/2021 | Katra | |
| 2021/0321912 A1 | 10/2021 | Katra | |

FOREIGN PATENT DOCUMENTS

| | | |
|---|---|---|
| WO | 2003077761 A1 | 9/2003 |
| WO | 2011159148 A2 | 12/2011 |
| WO | 2012005696 A1 | 1/2012 |

OTHER PUBLICATIONS

Blackwell, et al., "In Vivo Time-Resolved Autofluorescense Measurements to Test for Glycation of Human Skin", University of California Postprints, Jan.-Feb. 2008, Paper 2665.

Carneiro, "Haemoglobin and haematocrit: is the threefold conversion valid for assessing anaemia in malariaendemic settings", Malaria Journal May 22, 2007, 6:67.

Ciobanu, et al., "Fiuorophores advanced glycation end products (AGEs)-to-NADH ratio is predictor for diabetic chronic kidney and cardiovascular disease", J Diabetes Complications. Sep.-Oct. 29, 2015 (7):893-7. doi: 10.1016/j.diacomp.2015.06.006. Epub Jun. 16, 2015.

De Den Us, et al., "Temporal Variations in Hematocrit Values in Patients with Left Ventricular Dysfunction: Relationship with Cause-Specific Mortality and Morbidity and Optimal Monitoring-Further Insights from SOLVD", Can. J . Cardiel, Jan. 2008, 24: 45-48.

Ediger, et al., "Noninvasive Optical Detection of Impaired Glucose Tolderance: A Comparison Against FPG and A1C", 62, Review of Endocrinology, Jun. 2007.

Hartog, et al., "Advanced glycation end-products (AGEs) and hearth failure: Pathophysiology and clinical Implications", European Journal of Heart Failure Dec. 2007, 1146-1155.

Horecker, "The Absorption Spectra of Hemoglobin and its Deriavitives in the Visible", Dec. 3, 1942.

International Search Report and Written Opinion of International Application No. PCT/IB2019/050235, mailed Apr. 26, 2019, 13 pp.

Jeon, et al., "Noninvasive Total Hemoglobin Measurement", Journal of Biomedical Optics, 7(1), Jan. 2020, 45-50.

Li, et al., "Advanced glycation end products bisphasicallu modulate bone resorption in osteoclast-like cells", Am J Physiol Endocrinol Metab 310: E355-E366, 2016.

Lown Des, "Blood interference in fluorescence spectrum—Experiment, analysis and comparison with intra-operative measurements on brain tumor", Linkoping University, Jul. 9, 2010, 42 pages.

McMurdy, et al., "Noninvasive Optical, Electrical, and Acoustic Methods of Total", Clinical Chemistry 54:2, 264-272 (2008).

Pandey, et al., "Emerging trends in optical sensing of glycemic markers for diabetes monitoring", Trends Analyt Chem. Jan. 1, 2015; 64: 100-108.

Prosecution History from U.S. Appl. No. 15/866,036, dated Jul. 2, 2020 through May 12, 2021, 55 pp.

Prosecution History from U.S. Appl. No. 15/866,118, dated Jul. 30, 2020 through Oct. 1, 2021, 73 pp.

Prosecution History from U.S. Appl. No. 15/866,160, dated Jun. 29, 2020 through May 12, 2021, 34 pp.

Rabe, et al., "Measurement of Transcutaneous Hemoglobin Concentration by Noninvasive White-Light Spectroscopy in Infants", Pediatrics, Oct. 2005, vol. 116/Issue 4 (abstract).

Wong, et al., "Augmentation of the Neutrophil Respitory Burst Through the Action of Advanced Glycation End Products", Diabetes Sep. 2002; 51(9): 2846-2853.

Notification of Transmittal of the International Search Report and the Written Opinion of the International Searching Authority, or the Declaration for PCT/IB2019/050235.

Notification of Transmittal of the International Search Report and the Written Opinion of the International Searching Authority, or the Declaration for PCT/182019/050236 mailed Apr. 26, 2019.

Notice of Allowance from U.S. Appl. No. 17/352,649 dated Oct. 30, 2023, 5 pp.

Response to Office Action dated Jun. 30, 2023 from U.S. Appl. No. 17/352,649, filed Oct. 2, 2023, 12 pp.

International Search Report and Written Opinion of International Application No. PCT/IB2019050238 dated Jun. 26, 2019, 12 pp.

Office Action from U.S. Appl. No. 17/352,649 dated Jun. 30, 2023, 13 pp.

Office Action from U.S. Appl. No. 17/365,719 dated Dec. 4, 2023, 10 pp.

Response to Office Action dated Dec. 4, 2023 from U.S. Appl. No. 17/365,719, filed Mar. 4, 2024, 10 pp.

(56) References Cited

OTHER PUBLICATIONS

Notice of Allowance from U.S. Appl. No. 17/365,719 dated Jun. 14, 2024, 5 pp.
Response to Final Office Action dated Mar. 29, 2024 from U.S. Appl. No. 17/365,719, filed May 28, 2024, 9 pp.
Final Office Action from U.S. Appl. No. 17/365,719 dated Mar. 29, 2024, 11 pp.

* cited by examiner

SYSTEM AND METHOD FOR NON-INVASIVE MONITORING OF HEMATOCRIT CONCENTRATION

RELATED APPLICATION

This application is a continuation of U.S. application Ser. No. 15/866,118, filed Jan. 9, 2018, the entire content of which is incorporated herein by reference.

TECHNICAL FIELD

This disclosure relates generally to patient diagnosis and monitoring, and in particular to non-invasive diagnosis and monitoring of patient hematocrit levels.

BACKGROUND

Hematocrit refers to the volume percentage of red blood cells in blood. Because red blood cells are responsible for the transfer of oxygen from the lungs to body tissue, a patient's hematocrit may be utilized to determine the capability of delivering oxygen. In addition, hematocrit measurements are useful in diagnosing patient conditions, such as anemia, in which a patient has too few red blood cells.

Various methods exist for measuring hematocrit. In general, these methods require analyzing a blood sample in vitro. Typically, a patient visits a healthcare facility and has blood drawn and sent to a lab for analysis, which may include using automated equipment to analyze the sample, using one or more well-known methods. For example, blood samples may be analyzed using spectroscopy techniques, centrifugal techniques in which the sample is put in a centrifuge to separate the blood sample into its various components (red blood cells (RBCs), white blood cells (WBCs), platelets, plasma, etc.). However, each of these techniques requires the patient to have blood drawn and provided to a lab for in vitro analysis. This requires the patient to visit a healthcare facility each time a blood sample is to be analyzed.

It would therefore be advantageous to develop a device that is capable of non-invasively monitoring hematocrit levels in vivo over a period of time.

SUMMARY

According to one embodiment, a method of non-invasively monitoring hematocrit levels includes providing incident light to patient tissue at a first excitation wavelength to generate an emission response. The method further includes monitoring the emission response at a first wavelength and monitoring the emission response at a second wavelength. A ratiometric value is calculated based on a ratio of the emission response monitored at the first wavelength to the emission response generated at the second wavelength, wherein the hematocrit level is determined based on the calculated ratiometric value.

According to another embodiment, a system for non-invasive monitoring of hematocrit levels includes a medical device and a processing module. The medical device includes at least one light emitter and at least two photodetectors. The at least one light emitter is configured to provide a first excitation signal to patient tissue at a first wavelength selected to generate an emission response for a selected blood component. The at least two photodetectors are configured to monitor amplitudes of an emission response at a first emission wavelength and at a second emission wavelength, wherein the first emission wavelength is selected to correspond with a maximum of the emission response and the second emission wavelength is selected to correspond with a minimum of the emission response. The processing module is configured to receive emission response amplitudes measured at the first emission wavelength and the second emission wavelength, wherein the processing module calculates a ratiometric value based on the received emission responses and utilizes the calculated ratiometric value to determine the hematocrit level.

DETAILED DESCRIPTION

The present disclosure provides a system and method of in vivo measurement of hematocrit in patients. In some embodiments, the patient is equipped with one or more of an implantable device, insertable device, injectable device, or adherent device at a healthcare facility (e.g., doctor's office), referred to generally as patient medical devices. The patient devices include at least one light source for emitting light into the adjacent patient tissue (i.e., providing excitation), at least one photodetector for detecting the emission response of the tissue (e.g., as a result of autofluorescence, absorption, reflectance, transmittance, etc. of the excitation provided). Based on the monitored emission response, a baseline ratiometric value is calculated. In some embodiments, a blood sample is also drawn from the patient at approximately the same time as the baseline ratiometric value is calculated and utilized to measure a hematocrit level. The baseline ratiometric value is associated with the lab-based hematocrit measurement. Periodically, the patient device utilizes the one or more light sources and one or more photodetectors to calculate a ratiometric value. Subsequent ratiometric values are compared to the baseline ratiometric value to estimate hematocrit levels. One benefit of this system and method, is that subsequent hematocrit measurements may be taken without requiring the patient to return to the doctor's office. As a result, patient's hematocrit levels may be monitored remotely over a period of time. In some embodiments, the monitored hematocrit levels are utilized to detect and/or diagnose patient conditions. For example, anemia may be diagnosed by monitoring whether the hematocrit level decreases below a threshold value.

Figure 1:
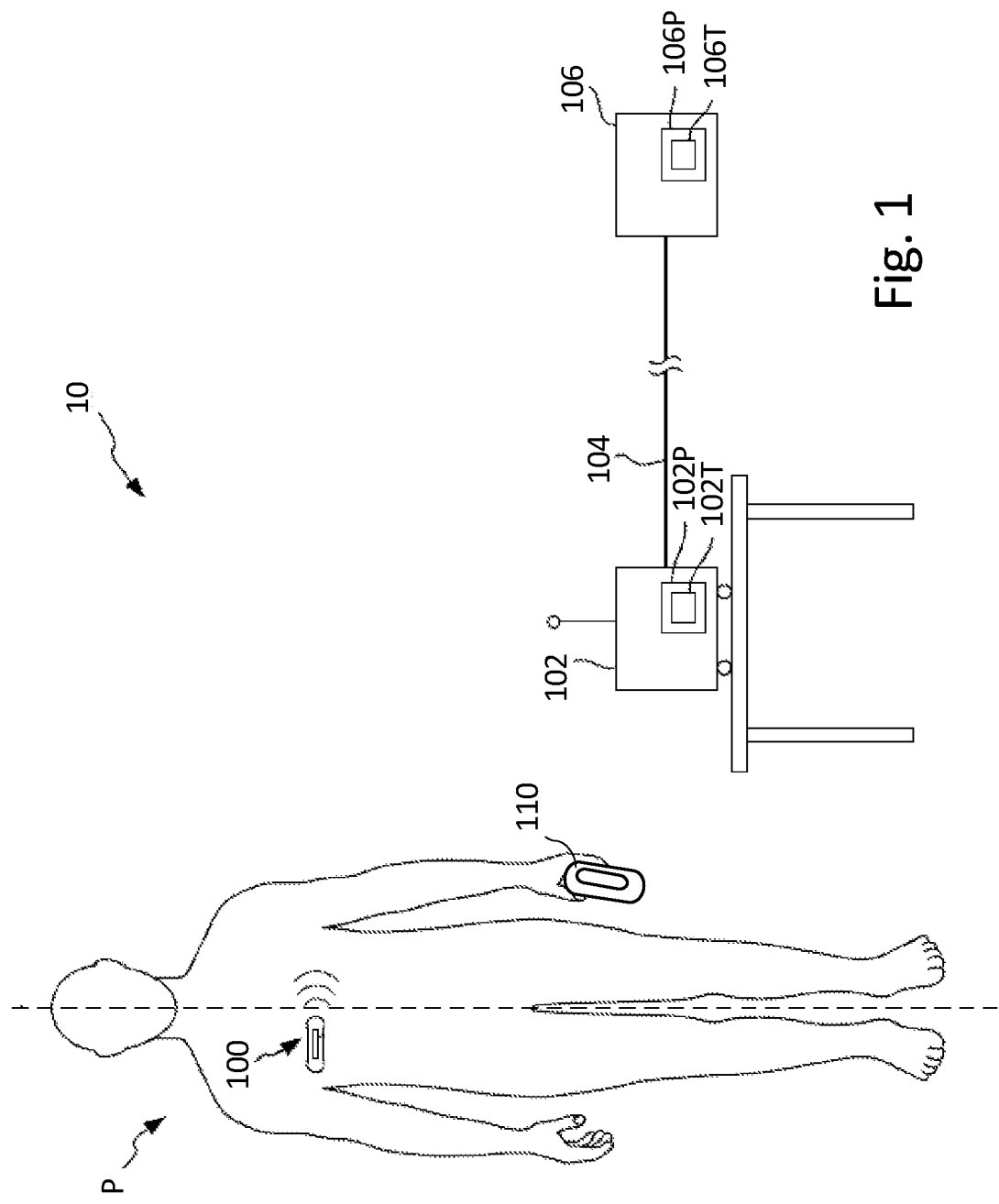
FIG. 1 illustrates a schematic view of a patient and a patient monitoring system, according to some embodiments.

FIG. 1 illustrates a patient P and a monitoring system 10 for non-invasive monitoring of hematocrit levels. In the embodiment shown in FIG. 1, monitoring system 10 comprises a patient medical device 100 and/or 110, gateway 102, and remote monitoring center 106. In the embodiment shown in FIG. 1, patient medical device 100 is an adherent device that attaches to the skin of the patient, and patient medical device 110 is a clip that fits over a patient's finger. In other embodiments, patient medical device may include implantable devices, insertable devices, injectable devices, arm cuff (similar to a blood pressure cuff) and/or wearable devices such as a Holter monitor (collectively referred to as a medical device). The medical device may be affixed to the skin of the patient, subcutaneously, or implanted adjacent to the tissue to be excited. In each example, the patient medical device utilizes optical components to monitor hematocrit levels of the patient. In some embodiments, patient medical device 100 and/or 110 includes one or more additional sensors for monitoring one or more additional physiological parameters of the patient, such as activity, orientation, cardiac activity, hydration, etc.

In the embodiment shown in FIG. 1, medical device 100 is adhered to the thorax of patient P, which allows for the monitoring of additional physiological parameters, such as ECG, hydration, activity, etc. In many embodiments, the device may adhere to one side of the patient, from which side data can be collected. A benefit of utilizing an adherent device, implantable, injectable, and/or wearable device is that it may be utilized to collect physiological data from the patient while the patient goes about normal day-to-day activities outside of a hospital setting. A medical device clipped to a patient's finger, such as medical device 110, is not worn throughout the day by a patient, but may be useful in applications such as these due to the relative ease in applying the clip to a patient's finger in order to take a reading. That is, rather than wearing the device for an extended period of time, a patient may periodically clip the device to the patient's finger for a few moments (e.g., seconds) in order to non-invasively measure a hematocrit level, and then removed. In some embodiments, hematocrit monitoring may be done on a weekly basis, daily basis, hourly basis, etc. The interval with which hematocrit levels are measured is based, in part, on the conditions/diseases to be monitored. For example, anemia monitoring may require only daily monitoring of hematocrit levels. In other embodiments, more frequent monitoring of hematocrit levels may be desired.

As discussed above, in some embodiments, the medical device may monitor a number of physiological parameters associated with patient P, including optical signals utilized to determine hematocrit levels, electrocardiogram (ECG) signals utilized to detect rhythm abnormalities such as tachycardia and/or bradycardia as well as activity level data, posture, bio-impedance, blood pressure (associated with a blood pressure cuff), etc. Analysis of one or more of these physiological parameters may be done locally by the medical devices 100 or 110, or remotely by gateway 102 and/or remote monitoring center 106 (or similar platform separate from the local medical device 100). Non-invasive monitoring of hematocrit levels relies on one or more optical sensors positioned on the medical device to provide one or more excitation sources (e.g., light) to patient tissue and monitor the emission response (e.g., light emitted by the patient tissue as a result of reflection, fluorescence, absorbance of the incident light). For example, in one embodiment one or more light sources associated with the medical device direct incident light to patient tissue. In addition, one or more photodetectors associated with the medical device measures the emission response of the tissue provided in response to the incident light (i.e., excitation source) at a particular emission wavelength. The photodetector converts the measured emission (i.e., optical signal) to an electrical signal that is representative of the amplitude or strength of the emitted light. As discussed in more detail below, analysis of the detected optical signal can be utilized to monitor hematocrit levels. In some embodiments, the analysis is performed locally by the medical device 100 or 110, while in other embodiments the monitored optical signal is transmitted to a gateway 102 or remote center 106 for analysis to detect hematocrit levels.

In one embodiment, gateway 102 comprises components of the zLink™, a small portable device similar to a cell phone that wirelessly transmits information received from medical device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent devices 100 or 110 are read by human experts to verify accuracy. Reports may then be generated at remote monitoring center 106 for communication to the patient's physician or care provider. As discussed above, in other embodiments gateway 102 may be implemented with a user device such as a smartphone, tablet, or computer capable of storing and executing one or more applications capable of processing data received from medical devices 100 and/or 110, as well as communicating the received data to remote monitoring center 106.

In an exemplary embodiment, the monitoring system comprises a distributed processor system with at least one processing module (not shown) included as part of adherent device 100 and/or 110, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters—including optical signals—monitored by medical device 100 and/or 110 may be analyzed by one or more of the distributed processors included as part of medical device 100 and/or 110, gateway 102, and/or remote monitoring center 106.

Figure 2A:
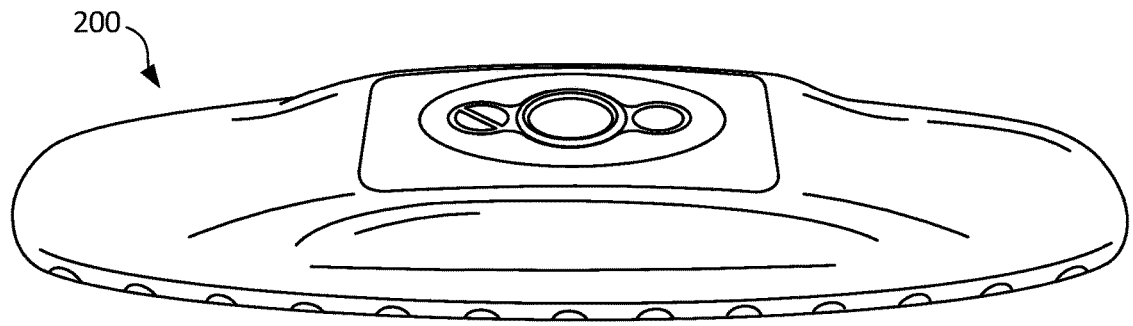
FIGS. 2A-2C are perspective views of an adherent monitoring device according to some embodiments.
Figure 2B:
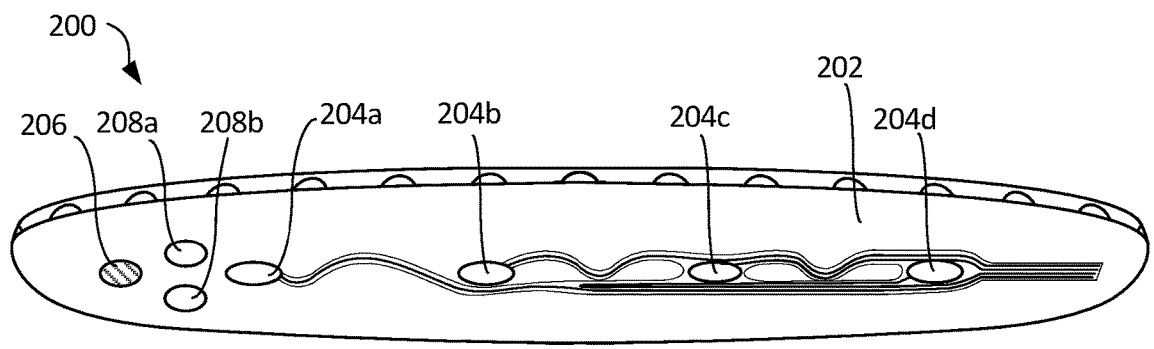
Figure 2C:
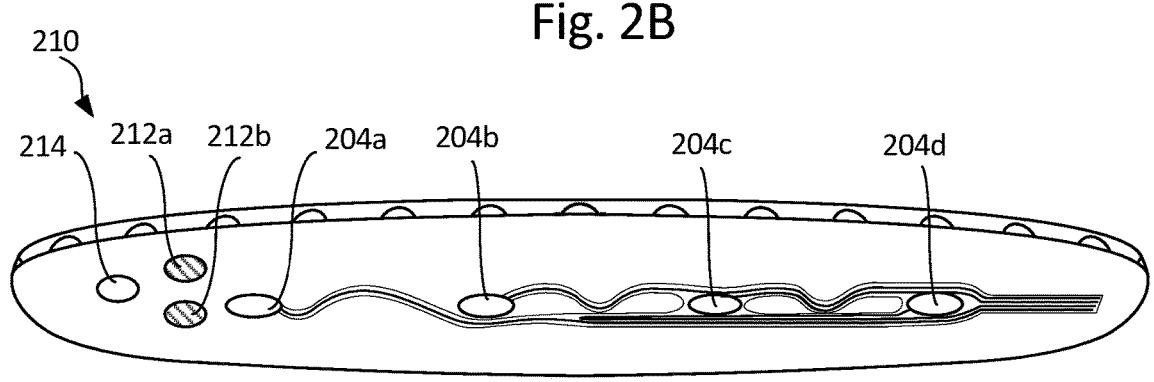

FIGS. 2A-2C are perspective views of an adherent monitoring device according to some embodiments. Adherent devices are adhered to the skin of a patient, and include one or more sensors utilized to monitor physiological parameters of the patient. Adherent devices are often-times utilized for long-term monitoring of ambulatory patients, allowing physiological parameters of the patient to be monitored over a period of time (e.g., days, weeks, months). Adherent devices therefore allow for both long-term monitoring of patients with chronic conditions (e.g., diabetes, heart failure, anemia, etc.) as well as monitoring and detection of acute incidences (e.g., carbon monoxide poisoning, blood loss, etc.), and can be utilized to provide dynamic monitoring (e.g., monitoring in response to a trigger or detected condition). This is in contrast with typical blood/tissue tests, which require blood be drawn by a lab and therefore do not allow for either long-term monitoring or detection of acute conditions.

The adherent device 200 illustrated in FIG. 2A illustrates the relatively low profile of adherent devices, which allows patients to wear the devices comfortably over a long period of time.

In the embodiment shown in FIG. 2B, a bottom surface 202 of adherent device 200 is shown, which includes a plurality of electrodes 204a-204d, at least one emitter 206, and one or more photodetectors 208a, 208b (two photodetectors shown in this embodiment). Electrodes 204a-204d are utilized to monitor electrical activity associated with the patient, including monitoring electrocardiogram (ECG) information and bio-impedance. The at least one light emitter 206 is utilized to generate excitation signals (e.g., incident light) at one or more excitation wavelengths. Different wavelengths of light may be selected in order to generate a particular emission response, which refers to how the incident light at a particular wavelength interacts with the various components of blood and/or tissue via reflectance, absorbance, fluorescence, etc., which is represented by the light emitted from the patient. For example, hemoglobin (Hb) is defined by an emission response to incident light provided at a particular wavelength, and as a major component of red blood cells (RBC) is useful in monitoring in order to determine hematocrit level.

In addition, the embodiment shown in FIG. 2B, the bottom surface 202 of adherent device 200 includes one or more photodetectors 208a, 208b (e.g., two photodetectors in the example shown in FIG. 2B). In this embodiment, photodetectors 208a, 208b are located in the same plane as emitter 206, but in other embodiments may be located opposite emitter 206. The emission response—which is generated at a result of absorption, transmittance, reflectance, and autofluoresence within the tissue—is therefore dependent on the location of the photodetectors 208 relative to the emitter 206. Therefore, the location of the photodetectors 208 relative to emitters 206 must be known.

As discussed above, typical spectral analysis requires monitoring the entire spectral response (e.g., all wavelengths) of an emission response. This is cost prohibitive though for implantable, adherent, injectable, and/or insertable medical device. Instead of monitoring all wavelengths, the embodiment shown in FIG. 2B selects one or more wavelengths to monitor. The wavelengths are selected based on the particular blood component being analyzed. For example, hemoglobin (Hb) emission responses have a well-known morphology, with maximum and minimum values occurring at known emission wavelengths. By measuring the amplitude of the emission response at a known maximum emission response and also at a known minimum, a ratiometric value is calculated using a ratio of the measured values. A benefit of utilizing a ratio is that the measure is relatively immune to noise and external factors such as change in ambient light intensity, molecule concentrations, artifacts, light source instability, detector instability, and/or changes in placement of the sensor. In this way, ratiometric values measured at a first instance can be compared to ratiometric values measured at subsequent instances in time and compared, despite the absolute values of the measured emission amplitudes changing.

As discussed above, assuming emission wavelengths are selected at minimums and maximums associated with the known Hb morphology, the ratiometric value is utilized to determine Hb levels, but alone cannot be utilized to determine hematocrit levels without information regarding the levels of the other blood components (e.g., plasma, white blood cells (WBCs), platelets, etc.). In some embodiments, a baseline ratiometric value is taken and associated with a known hematocrit level of the patient, wherein subsequent ratiometric values are compared to the baseline ratiometric value to determine the hematocrit level. In other embodiments, one or more additional ratiometric values are captured related to one or more other components of hematocrit (e.g., plasma, WBCs, platelets, etc.) and the combination of the measured blood component levels is utilized to determine hematocrit level.

In addition, because Hb exists in both an oxygenated state and deoxygenated state—each of which exhibits a different emission morphology—in some embodiments emission wavelengths are selected to correspond with isosbestic points associated with the oxy-Hb and deoxy-Hb emission responses. In some embodiments, both the first emission wavelength selected for monitoring and the second emission wavelength selected for monitoring correspond with isosbestic points, wherein a first emission wavelength corresponds with a maximum isosbestic point and a second emission wavelength corresponds with a minimum isosbestic point. The utilization of isosbestic points negates transitory changes in oxy-Hb and deoxy-Hb concentrations, while constructing a ratio out of a maximum isosbestic point and a minimum isosbestic point negates external noise factors (e.g., changes in ambient light conditions, etc.).

Although in the embodiment shown in FIG. 2B, a single emitter 206 is shown along with a pair of detectors 208a and 208b, additional emitters may be utilized along with additional or fewer detectors (e.g., a single detector utilized in combination with a pair of emitters). In addition, although each emitter and detector is illustrated as a separate entity, in some embodiments the functions of an emitter and detector are included in a single device. Therefore, on one embodiment light source 206 may also include a photodetector 208. Photodetectors may be implemented with well-known imaging sensors such as CCD or CMOS image sensors.

In the embodiment shown in FIG. 2C, rather than utilize two or more detectors, adherent device 210 includes a single photodetector 214. In this embodiment, each light source or emitter 212a and 212b once again provides incident light at a unique wavelength selected to generate an emission response related to the blood component to be monitored. Photodetector 214 monitors emissions at a single wavelength, selected to correspond with a maximum of the emission response associated with the first excitation wavelength or the second excitation wavelength. For example, in one embodiment the first excitation wavelength is selected to provide a significant (e.g. maximized) first emission response associated with a blood component to be monitored, and photodetector 214 is selected to monitor an emission response wavelength associated with a maximum of the emission response (e.g., isosbestic point associated with oxy-Hb and deoxy-Hb). The second excitation wavelength is selected to provide a significant minimum emission response with respect to the blood component to be monitored, and photodetector 214 monitors the emission response at the same wavelength monitored with respect to the first emission response. In this embodiment, selective variation of the excitation wavelength creates the desired difference/ratio in the emission response.

In some embodiments, emitters 212a and 212b are controlled to generate incident light mutually exclusive of one another (e.g., one at a time). This allows detector 214 to measure the emission response associated with the first excitation wavelength and the emission response associated with the second excitation wavelength, separately. For example, in one embodiment emitter 212a is activated to provide incident light at a first excitation wavelength. Photodetector 214 measures an attribute (e.g., amplitude) relating to the emission response at a given emission wavelength. Subsequently, emitter 212a is deactivated and emitter 212b is activated to provide incident light at a second excitation wavelength. Photodetector 214 measures the attribute (e.g., amplitude) relating to the emission response at the same given emission wavelength. The ratio of the measured amplitudes is utilized to measure a blood concentration component and/or a blood concentration component level (e.g., Hg) relative to another blood concentration level (e.g., HbA1c).

In other embodiments, more than two light sources (e.g., emitters) may be utilized to provide incident light at more than two unique excitation wavelengths. In addition, more than a single photodetector may be utilized in order to measure attributes of the emission response at a plurality of emission wavelengths. Similarly, although a pair of emitters 212a and 212b and a single photodetector 214 are utilized in FIG. 2C, in other embodiments more than two emitters may be utilized along with a plurality of photodetectors. In addition, although each emitter and photodetector is illustrated as a separate entity, in some embodiments the functions of an emitter and photodetector are included in a single element.

Figure 3:
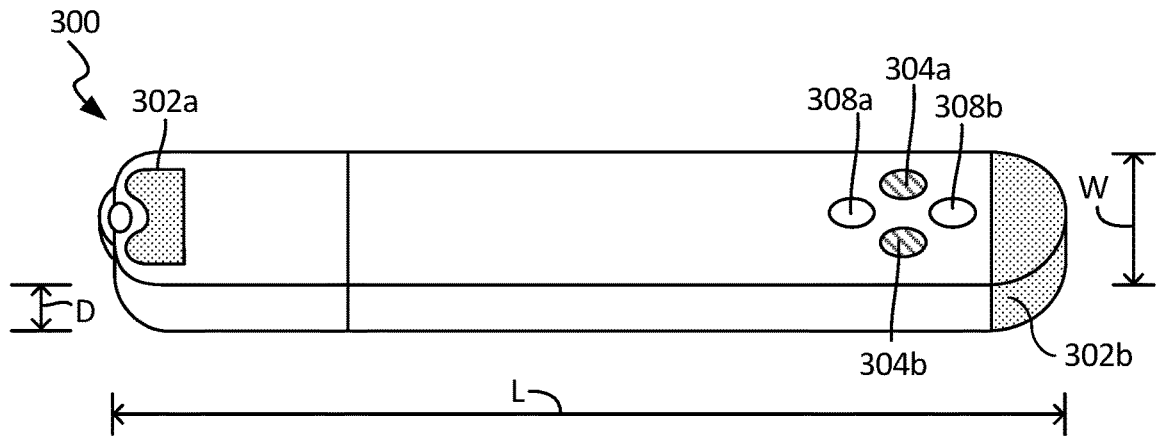
FIG. 3 is a perspective view of an insertable monitoring device according to some embodiments.

FIG. 3 is a perspective view of an insertable monitoring device 300 according to some embodiments. In contrast with an adherent device, which is secured to the skin of a patient, insertable monitoring devices 300 are inserted subcutaneously. Insertable device 300 includes at least first and second electrodes 302a and 302b, at least one light emitter 304 (emitters 304a and 304b are shown) and at least one photodetector 308 (photodetectors 308a and 308b are shown). As discussed above with respect to FIGS. 2B and 2C, insertable monitoring device 300 utilizes the at least one emitter to emit light at an excitation wavelength selected based on the blood component to be monitored (e.g., oxy-Hb, deoxy-Hb). The at least one photodetector 308 may be utilized to monitor one or more emission wavelengths, selected to correlate with maximums and/or minimums of the blood component to be monitored (e.g., oxy-Hb, deoxy-Hb, isosbestic points associated with oxy-Hb, deoxy-Hb, other blood components). As described with respect to FIGS. 2A-2C, emission response ratios can be created by selectively applying first and second excitation wavelengths to generate separate first and second emission responses. In other embodiments, the ratio can be created by selectively applying a single excitation wavelength and with respect to the emission response, utilizing a first emission wavelength and second emission wavelength to generate the desired ratio. In still other embodiments, one or more excitation sources may be applied in combination with monitoring of one or more emission wavelengths to generate a plurality of ratiometric values associated with one or more blood components to determine hematocrit levels.

As described above with respect to FIGS. 2A-2C, in some embodiments a baseline ratiometric value is measured and associated with a known hematocrit level (based on a blood sample hematocrit test). In this embodiment, the baseline ratiometric value is measured at approximately the same time as the hematocrit level is tested. For example, at the time of insertion of the insertable device 300 (typically in a physician's office, although not necessarily in a sterile setting), a blood sample may be taken and utilized to detect hematocrit rate. In other embodiments, due to issues of swelling of the tissue at the time of insertion of medical device 300, a baseline ratiometric measurement is taken several day or several weeks after insertion of the device 300 to negate the impacts of swelling/inflamed tissue at the site of the insertion. At approximately the same time the baseline ratiometric value is determined, a blood sample is taken to measure hematocrit level via a lab test. Subsequent ratiometric measurements can then be taken and compared to the baseline ratiometric value. Similarly, implanting an implantable device in a patient may require several days/weeks for the tissue surrounding the implanted device to heal before meaningful measurements can be taken.

Figure 4:
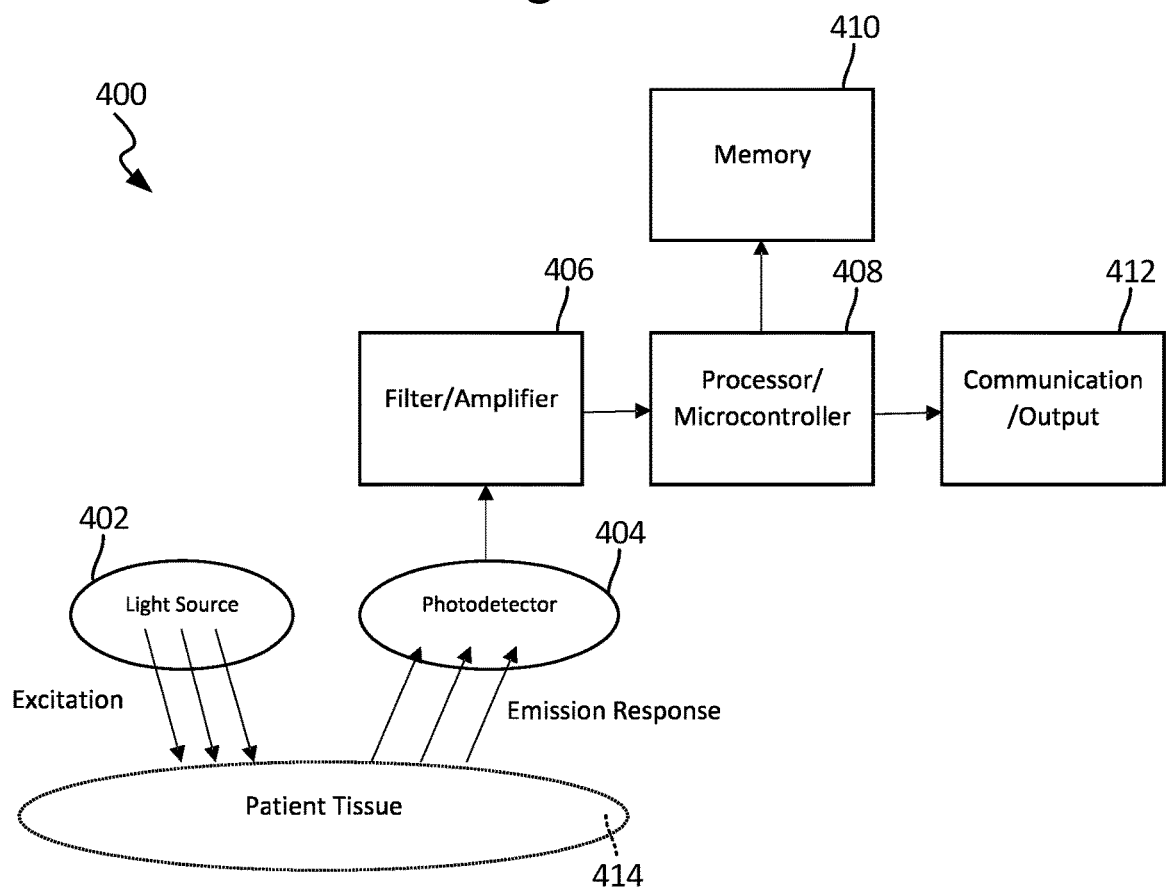
FIG. 4 is a block diagram illustrating components utilized to monitor optical signals and processing optical signals according to some embodiments.

FIG. 4 is a block diagram illustrating components utilized to monitor optical signals and processing optical signals according to some embodiments. Medical device 400 includes at least one light source 402, at least one detector 404, filter/amplifier 406, processor/microcontroller 408, memory 410, and communication/output 412. As described above, medical device 400 may be adhered to the patient's skin, clipped onto a patient's finger, attached via an arm cuff, inserted subcutaneously, or implanted within the patient. Light source 402 emits light that is provided incident to the patient's tissue, referred to herein as "excitation". In some embodiments, excitation may be provided at a plurality of wavelengths or at a selected wavelength. For example, the wavelength of the emitted light may be selected based on the blood component (e.g., particular protein such as oxy-Hb, deoxy-Hb, etc.) to be analyzed, wherein different wavelengths of light interact differently with particular proteins/lipids. In some embodiments, light source 402 includes a plurality of light sources each capable of emitting at a particular unique wavelength.

Light from light source 402 interacts with patient tissue 414. The interaction is a result of one or more processes, including autofluorescence, absorption, transmittance, reflectance, etc. that results in the emission of light from the tissue, referred to as the emission response. The emission response is detected by the one or more photodetectors 404. In the embodiment shown in FIG. 4, both the light sources 402 (emitters) and photodetectors 404 are located in the same optical plane. In other embodiments, photodetector 404 may be located opposite light source 402. For example, in a device attached to a patient's finger this type of configuration may be utilized, in which light transmitted on one side of patient tissue, is detected on the other side. The same principles of autofluorescence, absorption, transmittance, and reflectance apply, although the emission response "seen" by the photodetector 404 will vary based on the location of the photodetector relative to the light source 402.

In some embodiments, photodetector 404 may utilize well-known optical sensors, such as complimentary metal-oxide-semiconductor (CMOS) sensor or a charge-coupled device (CCD) sensor. Each of the one or more photodetectors 404 is configured to detect light at a particular emission wavelength. For embodiments in which a plurality of emission wavelengths are monitored, a plurality of photodetectors 404 are required, each configured to monitor one of the desired emission wavelengths. The emission wavelengths monitored by the one or more photodetectors 404 are selected based on the particular blood component being monitored. For example, the emission response morphology (i.e., amplitude of the emission response across the entire wavelength spectrum) depends on how light interacts with the blood component being monitored, with emission responses for each blood component providing different emission response morphology. In some embodiments, emission wavelengths monitored by the one or more photodetectors are selected to correspond with maximum and/or minimum values associated with the emission response spectrum being monitored. In some embodiments, emission wavelengths monitored by the one or more photodetectors correspond with isosbestic points associated with the one or more blood components being monitored (e.g., isosbestic point associated with oxy-Hb and deoxy-Hb). In some embodiments, a first isosbestic point corresponds generally with a maximum isosbestic value associated with the blood components being monitored and a second isosbestic point corresponds with a minimum isosbestic value associated with the blood components being monitored, providing a ratiometric value associated with the blood components to be monitored.

The one or more photodetectors convert the monitored optical signal (i.e., the emission response) to an electrical signal representative of the amplitude of the emission wavelength being monitored. Filter/amplifier 406 filters and amplifies the signal to provide a clean signal to processor/microcontroller 408.

Processor/microcontroller 408 operates in conjunction with memory 410 and communication output 412. In some embodiments, processor/microcontroller 408 provides the measured emission response signals monitored by the photodetectors to an intermediate gateway 102 and/or remote monitoring center 106 (shown in FIG. 1) for subsequent processing. In other embodiments, processor/microcontroller 408 executes instructions locally to perform analysis on the monitored emission response. This may include calculating ratiometric values associated with two or more monitored emission responses, calculating blood component concentrations based on the calculated ratios, comparing the ratios and/or blood component concentrations to threshold values, and/or storing calculated ratios and/or blood component concentrations to memory 410. Results of any analysis performed locally by processor/microcontroller may then be communicated to intermediate device 102, gateway 106, or provided as an alert to the patient (e.g., audio alert).

Figure 5:
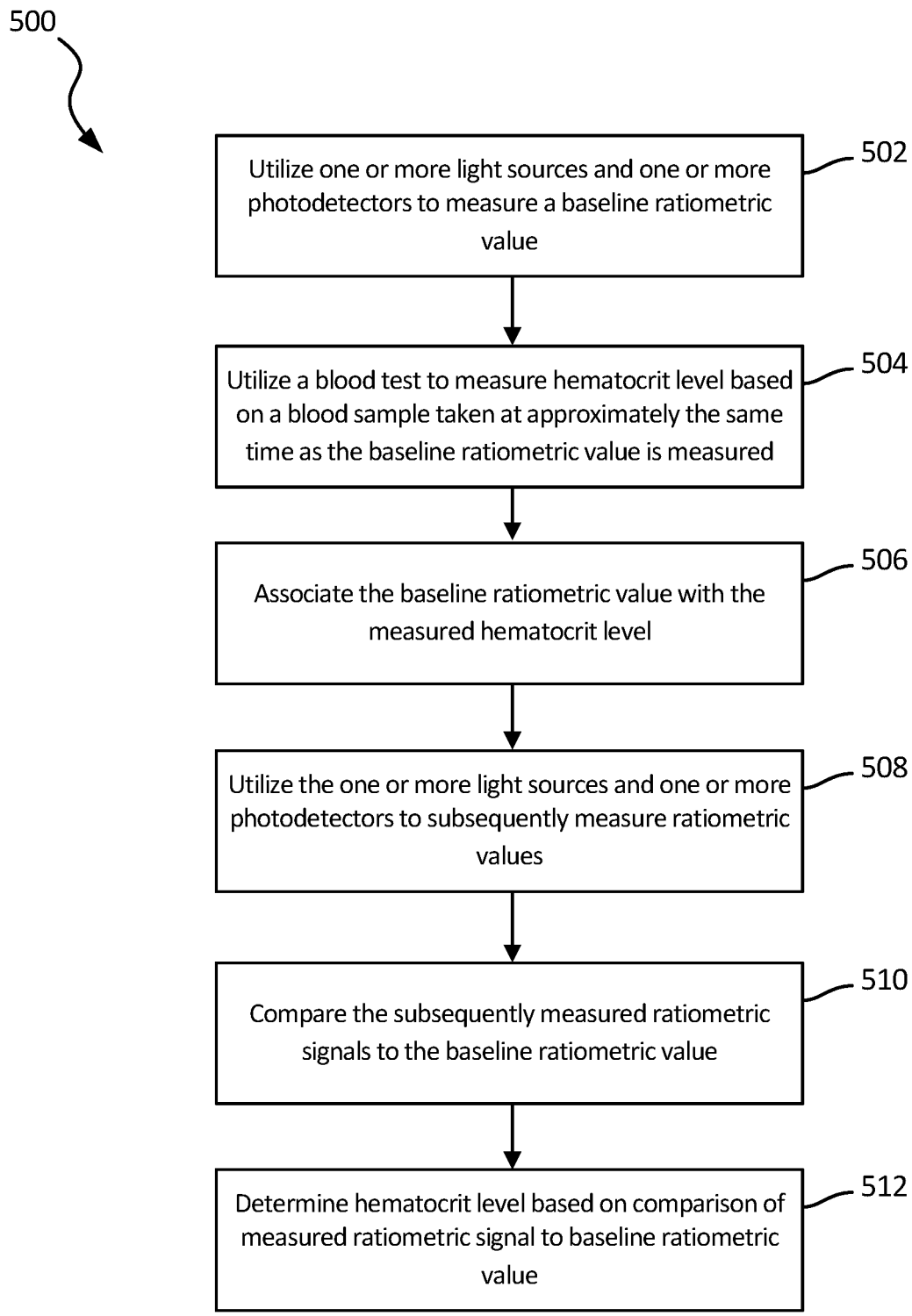
FIG. 5 is a flowchart that illustrates steps utilized to measure hematocrit levels according to some embodiments.

FIG. 5 is a flowchart that illustrates steps utilized to measure hematocrit levels according to some embodiments. At step 502, one or more light sources and one or more photodetectors are utilized to measure a baseline ratiometric value. In some embodiments, the one or more light sources provides an excitation source to the patient tissue selected to generate an emission response associated with a particular blood component to be monitored (e.g., RBCs, oxy-Hb, deoxy-Hb, etc.). In some embodiments, one or more photodetectors are utilized to monitor the emission response at one or more wavelengths. For example, in some embodiments, a first emission wavelength monitored corresponds with a known maximum response of the blood component to be monitored, while a second emission wavelength monitored corresponds with a known minimum response of the blood component to be monitored. An emission response amplitude is measured with respect to the first emission wavelength and with respect to the second emission wavelength, with the first and second amplitudes being utilized to form a baseline ratiometric value. In some embodiments, the first emission wavelength corresponds with a maximum isosbestic point for two or more blood components being monitored (e.g., oxy-Hb and deoxy-Hb). In addition, in some embodiment, the second emission wavelength corresponds with a minimum isosbestic point for the two or more blood components being monitored (e.g., oxy-Hb and deoxy-Hb), wherein the baseline ratiometric value is based on amplitudes measured with respect to the first and second isosbestic points.

In some embodiments, the baseline ratiometric value is stored locally by the medical device (e.g., medical device 100, 110, shown in FIG. 1). In other embodiments, the baseline ratiometric value is stored remotely (e.g., remote monitoring center 106 and/or gateway 102).

At step 504, hematocrit level of the patient is measured via a blood test. Any number of well-known methods of measuring hematocrit levels may be utilized, including centrifugal methods, spectroscopy methods, and others. In some embodiments, the blood sample utilized to measure the hematocrit level of the patient is performed at approximately the same time that the baseline ratiometric value is measured at step 502. For example, in one embodiment, the medical device is implanted, inserted, injected, or adhered to the patient and utilized to measure a baseline ratiometric value utilizing the one or more light source, and one or more photodetectors associated with the medical device. At approximately the same time, blood is drawn from the patient and utilized to measure hematocrit level via well-known lab-based techniques.

At step 506, the baseline ratiometric value measured by the medical device is associated with the measured hematocrit level, to create a reference value used as correction and/or correlation factor. The association between the baseline ratiometric value and the measured hematocrit may be stored locally on the medical device (e.g., medical device 100, 110) or may be stored remotely (e.g., remote monitoring system 106, gateway 102, etc.). In some embodiments, the association between measured hematocrit levels and baseline ratiometric values is stored at the same location responsible for subsequent analysis/processing of the measured ratiometric values.

At step 508, subsequent to measuring the baseline ratiometric value, the one or more light sources and one or more photodetectors associated with the medical device are utilized to measure a ratiometric value. The same technique utilized at step 502 to measure the baseline ratiometric value is utilized here to subsequently measure a ratiometric value. For example, if one or more particular excitation wavelengths are utilized to generate one or more emission responses and one or more particular emission wavelengths are monitored, the same excitation wavelength(s) and/or emission wavelengths are measured at step 508 to generate a ratiometric value that can be compared to the baseline ratiometric value.

At step 510, the hematocrit level of the patient is determined by comparing the subsequently measured ratiometric signal to the baseline ratiometric signal. In some embodiments, the baseline ratiometric value is stored locally on the medical device, and the comparison is performed locally on the medical device (e.g., medical device 100, 110). In other embodiments, the baseline ratiometric value is stored remotely at a monitoring system 106 and/or gateway 102, in which case the comparison is performed either at the remote monitoring system 106, and/or gateway 102.

In some embodiments, the calculation of hematocrit level is based on the difference between the baseline ratiometric value and the subsequently measured ratiometric value. For example, if the subsequently measured ratiometric signal is equal (or approximately equal) to the baseline raitometric signal, then the hematocrit level is approximately the same as that measured at the time the baseline ratiometric signal was measured. In some embodiment, in which the one or more excitation wavelengths and one or more emission wavelengths are selected to capture information related to RBCs (e.g., oxy-Hb and deoxy-Hb), then a decrease in the measured ratiometric signal indicates a decrease in RBCs and therefore a lower hematocrit level than that measured at the time the baseline ratiometric signal was measured. Similarly, an increase in the measured ratiometric signal indicates an increase in RBCs and therefore a higher hematocrit level than that measured at the time the baseline ratiometric signal was measured. In some embodiments, the amplitude of the difference between the baseline ratiometric value and the subsequently measured ratiometric value is utilized to quantitatively estimate the hematocrit level, while in other embodiments the change in hematocrit is noted.

At step 512, an alarm/communication is generated based on the determined hematocrit level (e.g., hematocrit level has fallen, indicating anemia). In some embodiments, the hematocrit level estimated at step 510 is communicated to a practitioner located at the remote monitoring center 106 for review. In other embodiments, an alert may be generated (e.g., audible, visible alert) by medical device (e.g., medical device 100, 110) to alert the patient of the condition. In some embodiments, the alert provides the patient with information including the estimated hematocrit level. In some embodiments, the alert provides the patient with instructions (e.g., call physician, schedule appointment, take medication, etc.). In some embodiments, a diagnosis may be provided to the patient based on the measured ratiometric signals and/or calculated hematocrit levels (e.g., anemia).

Figure 6:
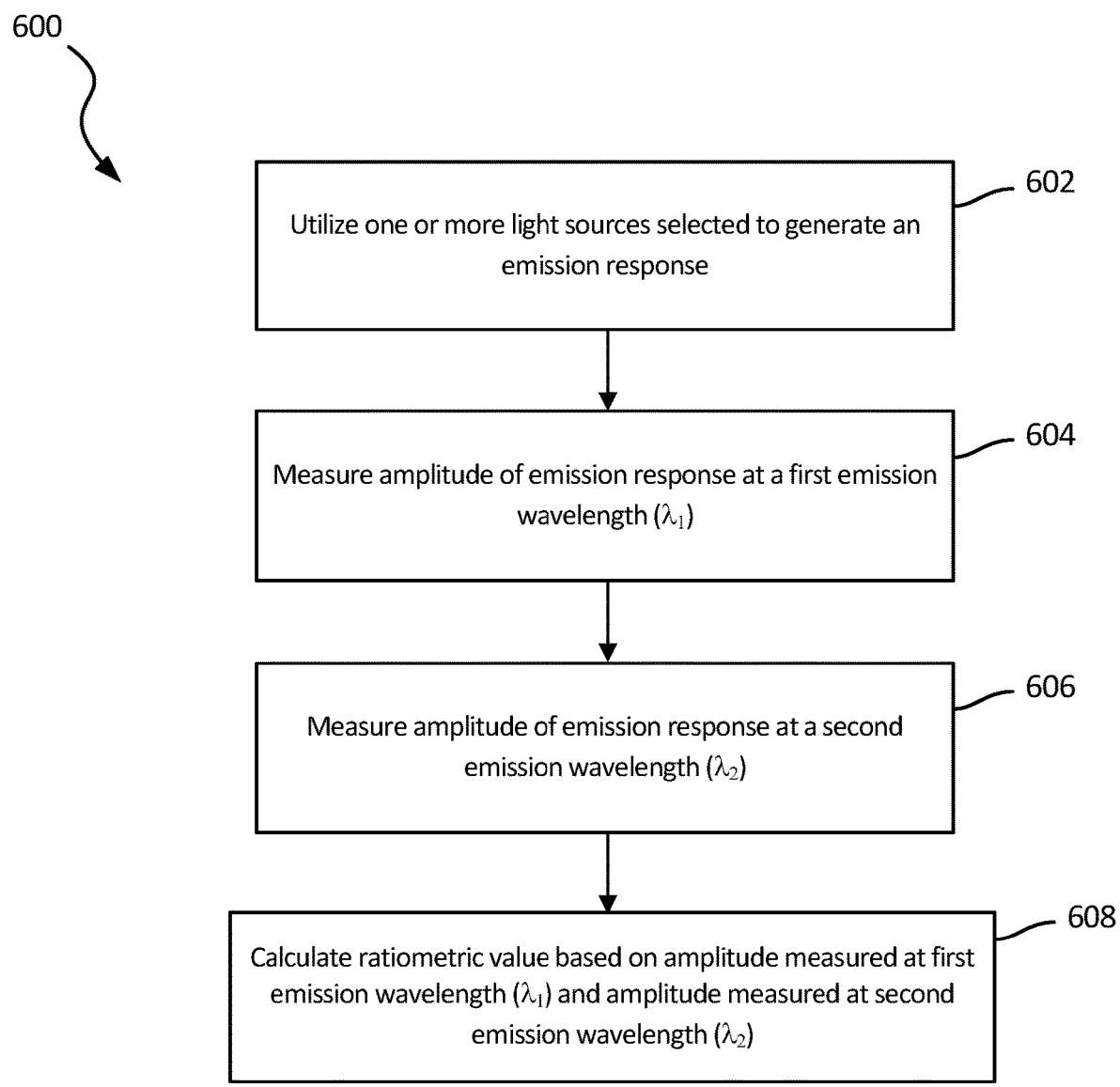
FIG. 6 is a flowchart that illustrates steps utilized to measure ratiometric values utilized to determine hematocrit levels according to some embodiments.
Figure 7:
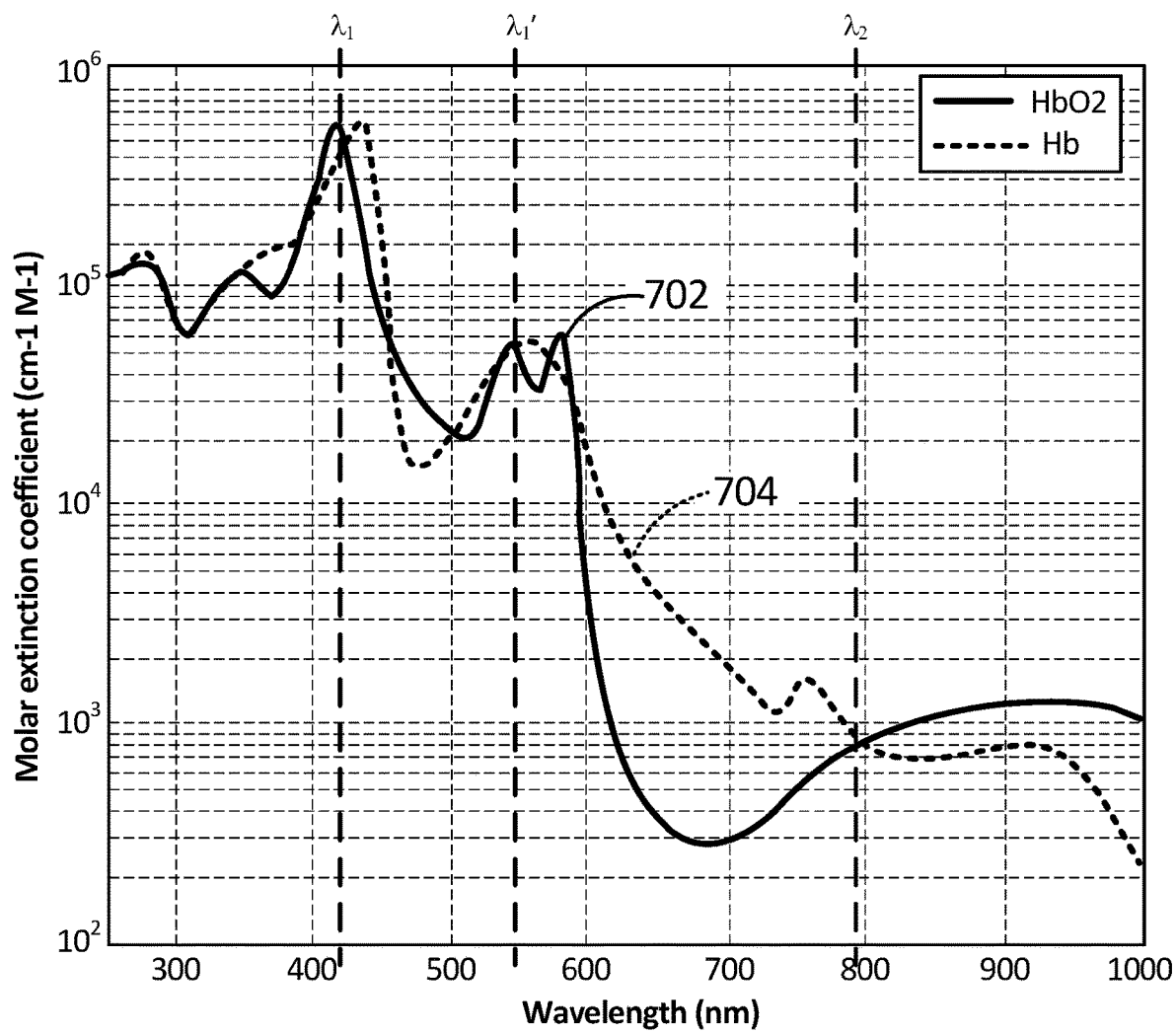
FIG. 7 is a graph that illustrates an emission response of blood and wavelengths monitored to measure the ratiometric value according to some embodiments.

FIG. 6 is a flowchart that illustrates steps 600 utilized to measure ratiometric values utilized to determine hematocrit levels according to some embodiments. FIG. 7 is a graph that illustrates an emission response of blood and wavelengths monitored to measure the ratiometric value according to some embodiments, and is utilized as an example to illustrate the method described with respect to FIG. 6. In particular, FIG. 7 illustrates the emission response of oxy-Hb and deoxy-Hb blood components, wherein oxy-Hb is illustrated by solid line 702 and deoxy-Hb is illustrated by dashed line 704.

At step 602, one or more light sources are utilized to generate one or more emission responses. As discussed above, in some embodiments a single excitation frequency is utilized to generate an emission response, and two or more photodetectors are utilized to monitor emission responses at two or more wavelengths. In other embodiments, however, two or more light sources may be utilized to generate two or more emission responses, with one or more photodetectors utilized to measure amplitudes of the emission response at one or more wavelengths. In the embodiment shown in FIGS. 6 and 7, a single light source is utilized to generate the emission response illustrated in FIG. 7. For example, in one embodiment the excitation wavelength of the first light source is in the infrared range (e.g., 700 nm to approximately 1 µm), although in other embodiments other excitation wavelengths (e.g., visible, ultra-violet spectrum) may be utilized so long as the emission response provides the desired morphology for the blood components to be monitored.

At step 604, a first amplitude is measured at a first emission wavelength $\lambda_1$. In some embodiments, the first emission wavelength $\lambda_1$ is selected to correspond with a maximum of the emission response. In other embodiments, in which two or more blood components are being targeted simultaneously, such as oxy-Hb and deoxy-Hb, the first wavelength $\lambda_1$ may be selected to correspond with a maximum isosbestic point associated with oxy-Hb and deoxy-Hb emission responses. For example, in the embodiment shown in FIG. 7, first emission wavelength $\lambda_1$ is approximately 420 nanometers (nm), which corresponds with a maximum isosbestic point. As shown in FIG. 7, a number of isosbestic points may be selected, as illustrated by first emission wavelength $\lambda_1'$ provided at a wavelength of approximately 550 nm. A benefit of utilizing an isosbestic point is that temporal variations in oxy-Hb and deoxy-Hb levels (changing with the patient's heart rhythm, exercise level, etc.) are minimized at isosbestic points as the emission response at these wavelengths is approximately the same for both oxy-Hb and deoxy-Hb. The first emission wavelength $\lambda_1$ may additionally be selected to minimize the emission response of other components of the patient's tissue, such as water, plasma, etc., in order to maximize the effect of hematocrit components such as oxy-Hb and deoxy-Hb.

At step 606, a second amplitude is measured at a second emission wavelength $\lambda_2$. In some embodiments, the second emission wavelength $\lambda_2$ is selected to correspond with a minimum of the emission response. In addition, in some embodiments the second wavelength $\lambda_2$ is selected to correspond with a minimum isosbestic point associated with the oxy-Hb and deoxy-Hb emission responses. For example, in the embodiment shown in FIG. 7, the second emission wavelength $\lambda_2$ is approximately 800 nm, which corresponds with a minimum isosbestic point for oxy-Hb and deoxy-Hb.

At step 608, a ratiometric value is calculated based on emission response amplitudes measured at a first emission wavelength $\lambda_1$ and second emission wavelength $\lambda_2$. For example, in some embodiments the ratiometric value is based on the amplitude measured at the first emission wavelength divided by the amplitude measured at the second emission wavelength, which in general should provide a ratiometric value greater than one that increases with increased concentrations of oxy-Hb and deoxy-Hb. Similarly, if the ratiometric value is based on on the amplitude measured at the second emission wavelength divided by the amplitude measured at the first emission wavelength, the ratiometric value will be less than one and will decrease with increased concentrations of oxy-Hb and deoxy-Hb. The method illustrated in FIGS. 6 and 7 would be utilized to measure the baseline ratiometric value as well as subsequent ratiometric values.

Figure 8:
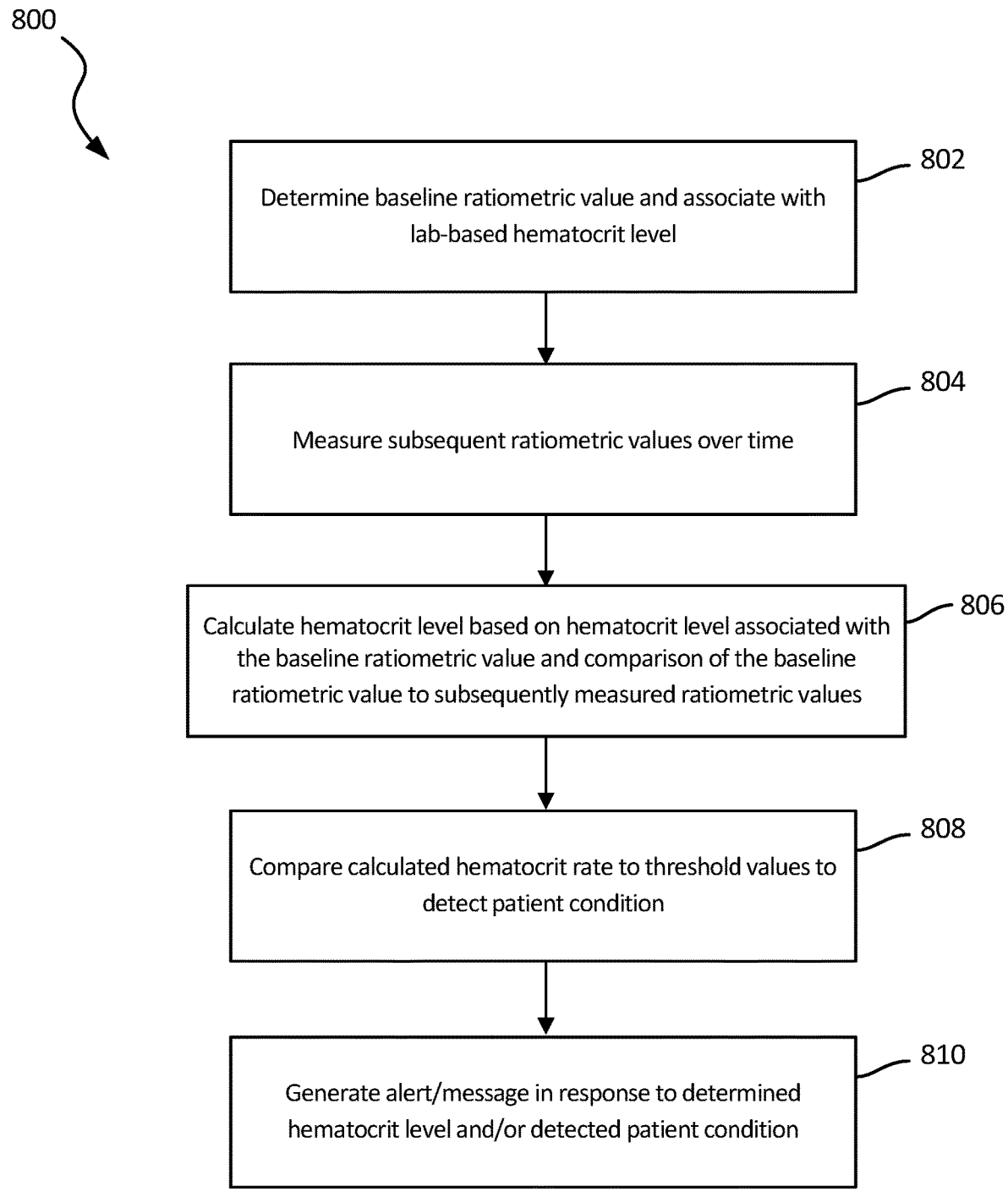
FIG. 8 is flowchart that illustrates steps utilized to detect and diagnose patient conditions according to some embodiments.

FIG. 8 is flowchart that illustrates steps 800 utilized to detect and diagnose patient conditions according to some embodiments. At step 802, one or more baseline ratiometric values are calculated and associated with lab-based hematocrit levels. In some embodiments, a single ratometric value may be calculated as described, for example, with respect to FIGS. 6 and 7 in which oxy-Hb and deoxy-Hb levels are determined using a combination of amplitudes measured at two emission wavelengths. In other embodiments, additional ratiometric values may be calculated with respect to a plurality of blood components (e.g., red-blood cells (RBCs), white-blood cells (WBCs), platelets, and plasma). A blood sample is utilized to measure the hematocrit level, with well-known methods of measuring a patient's hematocrit level being relied upon. As discussed above, measurement of hematocrit using a blood sample typically requires a patient to be physically present at a doctor's office or care facility to have blood drawn and provided to a lab for analysis.

At step 804, subsequent ratiometric values are measured using the same excitation wavelengths and emission wavelengths utilized to measure the baseline ratiometric value(s). Depending on the application, subsequent ratiometric values may be measured on a weekly basis, daily basis, hourly basis, or more frequently. For conditions like anemia, measuring ratiometric values on a daily basis is sufficient.

However, it may still be beneficial to take a number of measurements during a given day to generate an average value for detecting conditions like anemia. Other conditions, such as rapid blood loss caused by injury or bleeding may also be detected, but may benefit from more regular monitoring of measured ratiometric values. In contrast with the measurement of hematocrit level at step 802, in which a blood sample is required, subsequent measurements of ratiometric values does not require a patient to be present at a doctor's office or care facility. Rather, the subsequent ratiometric values may be measured while the patient undergoes normal activities remote from the doctor's office (e.g., at home, work, etc.).

At step 806, hematocrit levels are calculated based on comparisons of the baseline ratiometric value (associated with a known hematocrit level) and subsequently measured ratiometric values. In some embodiments, the association between the baseline ratiometric value and hematocrit level measured at approximately the same time is communicated to and stored locally on the patient medical device (e.g., medical device 100, 110). In other embodiments, the associated between baseline ratiometric value and hematocrit level is stored remotely (e.g., remote monitoring center 106 and/or gateway 102). In this embodiment, the calculation of hematocrit levels based on the subsequently measured ratiometric values and stored baseline ratiometric value is performed remotely either at remote monitoring center 106 and/or gateway 102.

Calculation of hematocrit levels may include quantifying hematocrit value, or may include calculating a hematocrit level relative to the lab-based hematocrit level (e.g., hematocrit level increasing/decreasing). For example, assuming the ratiometric value is expressed as the first emission wavelength $\lambda_1$ divided by the second emission wavelength $\lambda_2$, then a decrease in the subsequently measured ratiometric value indicates a decrease in hematocrit. In some embodiments, decrease in hematocrit is quantified based on the difference between the baseline ratiometric value and subsequently measured ratiometric value. In other embodiments, quantification of the decrease in hematocrit is not as important as identifying that the hematocrit is decreasing.

At step 808, the calculated hematocrit rate is utilized to detect conditions. For example, in some embodiments, if a patient suffers from anemia, identifying the decrease in hematocrit will result in a warning/alert being generated for the user to take medication to arrest the decline in hematocrit levels. In some embodiments, the calculated hematocrit rate is compared to threshold values to detect one or more conditions. For example, a patient may be identified as anemic if the calculated hematocrit level decreases below a threshold level. In some embodiments, the change in hematocrit level between the initial hematocrit level determined from a blood sample and the calculated hematocrit level is compared to a threshold level to a detect a change in patient condition. For example, this may be utilized to aid patients in taking medication or pre-diagnosis of diseases (such as anemia).

At step 810, alert and/or messages are generated in response to the detected patient condition. In some embodiments, the alert and/or message may simply include displaying the calculated hematocrit level to the patient and/or generating a message communicated to the care facility that includes the calculated hematocrit level. In other embodiments, the alert and/or messages includes more than the raw calculated hematocrit level. For example, in some embodiments an alert and/or message may be communicated to the patient, either via an auditory alert, visual alert, or combination thereof, instructing the patient to take some form of action (e.g., schedule a doctor' appointment, take medication, etc.). In other embodiments, the alert and/or message includes diagnosis or detection of a condition. For example, an alert and/or message may be generated indicating that the patient is anemic.

In some embodiments, ratiometric values are measured over a period of time (e.g., days, weeks, months) and utilized to monitor patient condition. In this way, patient condition may be monitored over a long period of time. In some embodiments, collected ratiometric values and/or calculated hematocrit levels are collected and stored, and utilized to generate one or more reports regarding patient condition.

Figure 9:
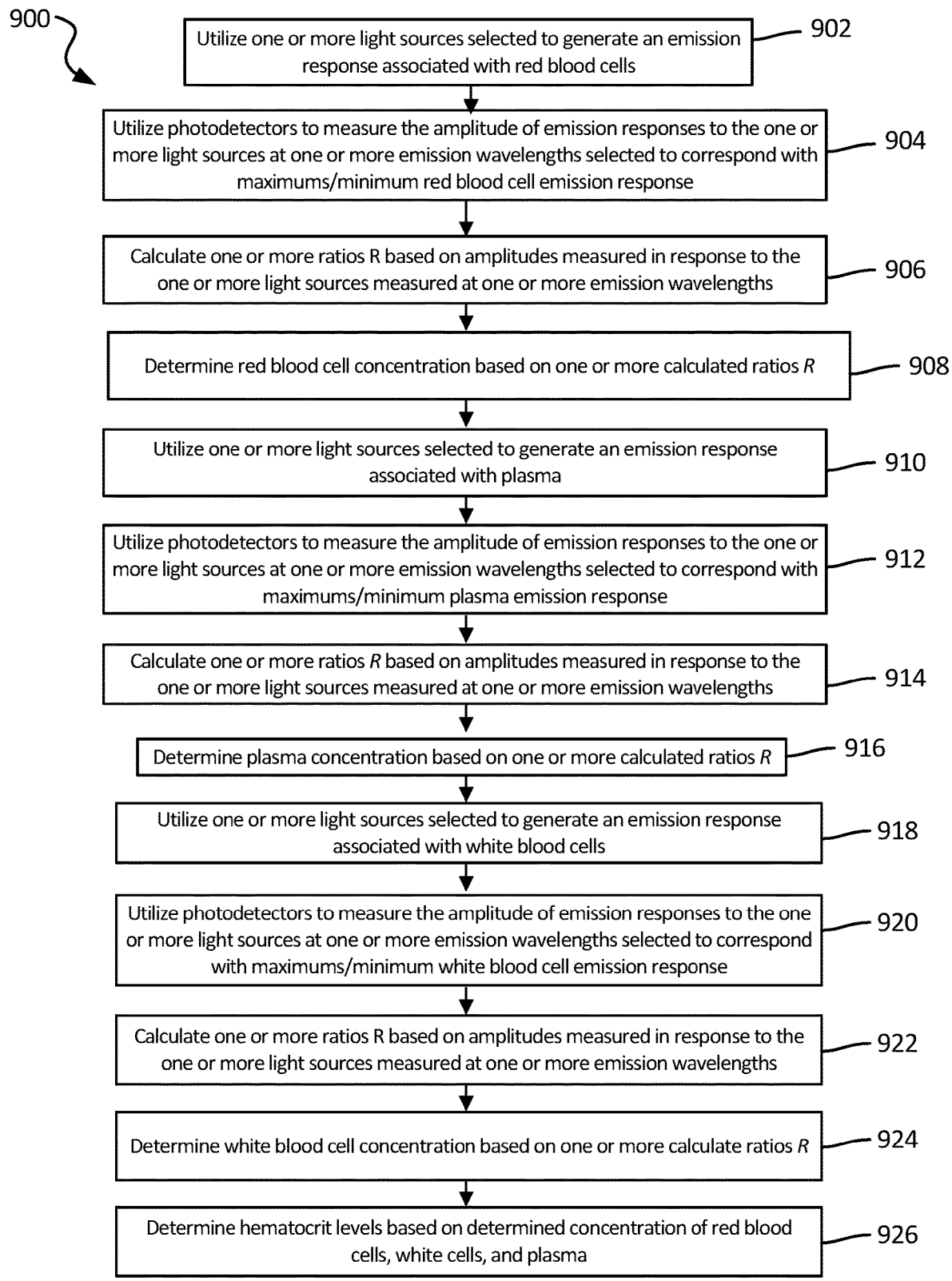
FIG. 9 is a flowchart that illustrates steps utilized to measure hematocrit levels according to some embodiments.

FIG. 9 is a flowchart that illustrates steps 900 utilized to measure hematocrit levels according to some embodiments. At step 902, one or more light sources are utilized to generate one or more emission responses. As discussed above, in some embodiments a single excitation frequency is utilized to generate an emission response, and two or more photodetectors are utilized to monitor emission responses at two or more wavelengths. In other embodiments, however, two or more light sources may be utilized to generate two or more emission responses, with one or more photodetectors utilized to measure amplitudes of the emission response at one or more wavelengths. For example, in one embodiment the excitation wavelength of the first light source is in the infrared range (e.g., 700 nm to approximately 1 μm), although in other embodiments other excitation wavelengths (e.g., visible, ultra-violet spectrum) may be utilized so long as the emission response provides the desired morphology for the blood components to be monitored.

At step 904, one or more photodetectors are utilized to measure the amplitude of the emission responses to the one or more light sources at one or more emission wavelengths selected to correspond with maximums/minimums of a first component of blood (e.g., red blood cells or components thereof such as oxy-Hb or deoxy-Hb). For example, as discussed above a first amplitude may be measured at a first emission wavelength, wherein the first emission wavelength is selected to correspond with a maximum of the emission response for the first component of blood. In other embodiments, in which two or more blood components are being targeted simultaneously, such as oxy-Hb and deoxy-Hb included in red blood cells, the first wavelength $\lambda_1$ may be selected to correspond with a maximum isosbestic point associated with oxy-Hb and deoxy-Hb emission responses. A benefit of utilizing an isosbestic point is that temporal variations in oxy-Hb and deoxy-Hb levels (changing with the patient's heart rhythm, exercise level, etc.) are minimized at isosbestic points as the emission response at these wavelengths is approximately the same for both oxy-Hb and deoxy-Hb. The first emission wavelength may additionally be selected to minimize the emission response of other components of the patient's tissue, such as water, other components of blood (e.g., white blood cells, platelets, plasma, etc.) in order to maximize the effect of the first component of blood being analyzed (e.g., red blood cells).

At step 906, one or more ratiometric values R are calculated based on the emission responses measured at step 904. For example, in some embodiments the ratiometric value is based on the amplitude measured at a first emission wavelength divided by the amplitude measured at the second emission wavelength. In other embodiments, it may be the amplitude measured in response to a first excitation source divided by the amplitude measured in response to a second excitation source.

At step 908, the concentration of the first blood component (e.g., red blood cells) is determined based on the one or more calculated ratios R. Determining the concentration of, for example, red blood cells does not alone provide information regarding the hematocrit, as the hematocrit requires knowledge of the concentration of red blood cells as a total volume of blood. To determine hematocrit, information regarding the concentration of other blood components (e.g. plasma, white blood cells, etc.) must be determined. At steps 910-924, the same method utilized to determine the concentration of red blood cells is utilized to determine the concentration of plasma and white blood cells.

In particular, at step 910 one or more light sources are utilized to generate one or more emission responses associated with plasma. As discussed above, in some embodiments a single excitation frequency is utilized to generate an emission response, and two or more photodetectors are utilized to monitor emission responses at two or more wavelengths associated with maximum/minimums of the particular emission response. In other embodiments, however, two or more light sources may be utilized to generate two or more emission responses, with one or more photodetectors utilized to measure amplitudes of the emission response at one or more wavelengths.

At step 912, one or more photodetectors are utilized to measure the amplitude of emission responses to the one or more light sources at one or more emission wavelengths selected to correspond with maximums/minimums of the plasma emission response. For example, this may include measuring amplitudes at a first emission wavelength and amplitudes at a second emission wavelength generated in response to a single excitation wavelength, wherein the first emission wavelength is associated with a maximum of the emission response for plasma and the second emission wavelength is associated with a minimum of the emission response for plasma.

At step 914, one or more ratios R are calculated based on the amplitudes measured with respect to the one or more emission responses. At step 916, the plasma concentration is determined based on the one or more calculated ratios. In some embodiments, because blood is comprised mostly of plasma and red blood cells, determining the red blood cell concentration and the plasma concentration is sufficient to generate an estimate of hematocrit level. That is, in some embodiments, steps 918-924 are skipped and hematocrit is estimated on the determined concentration of red blood cells and plasma. A benefit of this approach is it obviates the need for additional light sources and photodetectors selected to determine white blood cell concentrations, to the extent they differ from the wavelengths utilized to determine red blood cell concentration.

In embodiments in which white blood cell concentration is determined as well, then at step 918 one or more light sources are utilized to generate one or more emission responses associated with white blood cells. As discussed above, in some embodiments a single excitation frequency is utilized to generate an emission response, and two or more photodetectors are utilized to monitor emission responses at two or more wavelengths associated with maximum/minimums of the particular emission response. In other embodiments, however, two or more light sources may be utilized to generate two or more emission responses, with one or more photodetectors utilized to measure amplitudes of the emission response at one or more wavelengths.

At step 920, one or more photodetectors are utilized to measure the amplitude of emission responses to the one or more light sources at one or more emission wavelengths selected to correspond with maximums/minimums of a white blood cell emission response. For example, this may include measuring amplitudes at a first emission wavelength and amplitudes at a second emission wavelength generated in response to a single excitation wavelength, wherein the first emission wavelength is associated with a maximum of the emission response for white blood cells and the second emission wavelength is associated with a minimum of the emission response for white blood cells.

At step 922, one or more ratios R are calculated based on the amplitudes measured with respect to the one or more emission responses. At step 924, the white blood cell concentration is determined based on the one or more calculated ratios.

In this way, concentrations are determined for red blood cells, plasma and white blood cells. At step 926, the concentration of red blood cells, plasma and white blood cells are utilized to determine hematocrit level, wherein hematocrit is the ratio of red blood cells as compared with total blood volume (e.g., red blood cell concentration+plasma+white blood cells).

A benefit of the embodiment provided in FIG. 9 is that it provides a measure of actual hematocrit, rather than an estimation of hematocrit, at a cost of additional light sources and/or additional photodetectors.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system comprising:
a medical device comprising:
at least one light source configured to provide a first excitation signal to tissue of a patient, the first excitation signal configured to generate a continuous emission response spectrum from the tissue for at least two selected blood components; and
at least one light detector configured to receive the continuous emission response spectrum and detect a first emission response at a first emission wavelength and a second emission response at a second emission wavelength; and
one or more processors configured to:
calculate a ratiometric value based on a first emission response amplitude at the first emission wavelength and a second emission response amplitude at the second emission wavelength, wherein the first emission wavelength is selected to correspond with an isosbestic maximum associated with the at least two selected blood components of the continuous emission response spectrum and the second emission wavelength is selected to correspond with an isosbestic minimum associated with the at least two selected blood components of the continuous emission response spectrum, and the ratiometric value varies based on hematocrit level of the patient;
compare the calculated ratiometric value to a baseline ratiometric value;

determine a hematocrit level based on the comparison of the calculated ratiometric value to the baseline ratiometric value; and generate an alert of a condition of the patient based on the comparison.

2. The system of claim 1, wherein the one or more processors are configured to:

output the hematocrit level to a computing device.

3. The system of claim 1, wherein the baseline ratiometric value corresponds to a known baseline hematocrit level of the patient.

4. The system of claim 1, wherein the at least two selected blood components comprise oxygenated hemoglobin (oxy-Hb) and deoxygenated hemoglobin (deoxy-Hb).

5. The system of claim 1, wherein the medical device comprises the one or more processors.

6. The system of claim 1, further comprising a computing device configured to receive data from the medical device, wherein the computing device comprises the one or more processors.

7. The system of claim 1, wherein the medical device is an insertable monitoring device configured for subcutaneous insertion in the patient, wherein the medical device comprises a plurality of electrodes.

8. The system of claim 1, wherein the condition of the patient is anemia.

9. The system of claim 1, wherein the condition of the patient is heart failure.

10. An insertable monitoring device configured for subcutaneous insertion in a patient, the insertable monitoring device comprising:

communication circuitry configured to wireless communicate with an external computing device;

a plurality of electrodes;

at least one light source configured to provide a first excitation signal to tissue of a patient, the first excitation signal configured to generate a continuous emission response spectrum from the tissue for at least two selected blood components;

at least one light detector configured to receive the continuous emission response spectrum and detect a first emission response at a first emission wavelength and a second emission response at a second emission wavelength; and one or more processors configured to:

calculate a ratiometric value based on a first emission response amplitude at the first emission wavelength and a second emission response amplitude at the second emission wavelength, wherein the first emission wavelength is selected to correspond with an isosbestic maximum associated with the at least two selected blood components of the continuous emission response spectrum and the second emission wavelength is selected to correspond with an isosbestic minimum associated with the at least two selected blood components of the continuous emission response spectrum, and the ratiometric value varies based on hematocrit level of the patient;

compare the calculated ratiometric value to a baseline ratiometric value;

determine a hematocrit level based on the comparison of the calculated ratiometric value to the baseline ratiometric value; and control the communication circuitry to transmit an alert of a condition of the patient to the external computing device based on the comparison.

11. The insertable monitoring device of claim 10, wherein the one or more processors are configured to:

output the hematocrit level to the external computing device.

12. The insertable monitoring device of claim 10, wherein the baseline ratiometric value corresponds to a known baseline hematocrit level of the patient.

13. The insertable monitoring device of claim 10, wherein the at least two selected blood components comprise oxygenated hemoglobin (oxy-Hb) and deoxygenated hemoglobin (deoxy-Hb).

14. The insertable monitoring device of claim 10, wherein the condition of the patient is anemia.

15. The insertable monitoring device of claim 10, wherein the condition of the patient is heart failure.

16. A method comprising:

providing, by at least one light source of a medical device, a first excitation signal to tissue of a patient, the first excitation signal configured to generate a continuous emission response spectrum from the tissue for at least two selected blood components;

receiving, by at least one light detector of the medical device, the continuous emission response spectrum and detecting a first emission response at a first emission wavelength and a second emission response at a second emission wavelength;

calculating, by one or more processors, a ratiometric value based on a first emission response amplitude at the first emission wavelength and a second emission response amplitude at the second emission wavelength, wherein the first emission wavelength is selected to correspond with an isosbestic maximum associated with the at least two selected blood components of the continuous emission response spectrum and the second emission wavelength is selected to correspond with an isosbestic minimum associated with the at least two selected blood components of the continuous emission response spectrum, and the ratiometric value varies based on hematocrit level of the patient;

comparing, by the one or more processors, the calculated ratiometric value to a baseline ratiometric value;

determining, by the one or more processors, a hematocrit level based on the comparison of the calculated ratiometric value to the baseline ratiometric value; and generating, by the one or more processors, an alert of a condition of the patient based on the comparison.

17. The method of claim 16, further comprising outputting, by the one or more processors, the hematocrit level to a computing device.

18. The method of claim 16, wherein the baseline ratiometric value corresponds to a known baseline hematocrit level of the patient.

* * * * *